(12) United States Patent
Lloyd et al.

(10) Patent No.: US 6,890,300 B2
(45) Date of Patent: May 10, 2005

(54) IMPLANTABLE MICROSCALE PRESSURE SENSOR SYSTEM FOR PRESSURE MONITORING AND MANAGEMENT

(75) Inventors: John R. Lloyd, East Lansing, MI (US); Timothy A. Grotjohn, Okemos, MI (US); Arthur J. Weber, East Lansing, MI (US); Frank R. Rosenbaum, Haslett, MI (US); Gregory A. Goodall, Lake Orion, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/649,919

(22) Filed: Aug. 26, 2003

(65) Prior Publication Data

US 2004/0073137 A1 Apr. 15, 2004

Related U.S. Application Data

(60) Provisional application No. 60/406,169, filed on Aug. 27, 2002.

(51) Int. Cl.$^7$ .............................. A61B 3/16; A61B 5/00
(52) U.S. Cl. ....................................... 600/398; 600/561
(58) Field of Search ................................. 600/398–400, 600/405, 561, 587

(56) References Cited

U.S. PATENT DOCUMENTS

| | | | |
|---|---|---|---|
| 6,193,656 B1 * | 2/2001 | Jeffries et al. | 600/398 |
| 6,287,256 B1 * | 9/2001 | Park et al. | 600/398 |
| 6,447,449 B1 * | 9/2002 | Fleischman et al. | 600/405 |
| 6,579,235 B1 * | 6/2003 | Abita et al. | 600/398 |

* cited by examiner

*Primary Examiner*—Charles Marmor
(74) *Attorney, Agent, or Firm*—Ian C. McLeod

(57) ABSTRACT

A MEMS chip sensor (10, 20, 30, 40, 50, 60, 70) based upon detection of an induced inductance in the sensor is described. The sensor is used in an environment for detection of fluid pressures. The method and system is particularly used in animals, including humans, to sense pressure changes, particularly pressure in the eyeball.

29 Claims, 18 Drawing Sheets

Variations in the Placement of the Inductor Coil

IMPLANTABLE MICROSCALE PRESSURE SENSOR SYSTEM FOR PRESSURE MONITORING AND MANAGEMENT

CROSS-REFERENCE TO RELATED APPLICATION

This application claims priority to Provisional Patent Application No. 60/406,169 filed Aug. 27, 2002.

STATEMENT REGARDING FEDERALLY SPONSORED RESEARCH OR DEVELOPMENT

Not Applicable.
Reference to a "Computer Listing Appendix submitted on a Compact Disc"
Not Applicable.

BACKGROUND OF THE INVENTION

1. Field of the Invention

The present invention relates to a method and system which uses a MEMS chip wireless capacitive sensor containing an inductance coil and spaced apart capacitive plates, one of which is in pressure contact with a fluid. The sensor can be used in general applications and in animals, including humans, to sense pressure, particularly in the eye. In particular, the sensor is in contact with the fluid in the vitreous chamber adjacent the cornea or in the aqueous chamber adjacent to the cornea of the eye. The sensor preferably includes an external antenna.

2. Description of Related Art

The problems in monitoring eye pressure are exemplary of the general problems of pressure measurement in a living animal.

Intraocular Pressure In the Eye

Glaucoma is one of the most menacing diseases of the eye that exists today. Patients may suffer significant eye damage, including blindness, without experiencing a noticeable amount of pain or discomfort. Glaucoma is the second leading cause of blindness in the United States and is the leading cause of blindness among African Americans. There are several types of glaucoma; the most common of which is called primary open-angle glaucoma (POAG). POAG affects more than 3 million people with an additional 3–6 million Americans considered to be susceptible because they have one or more of the risk factors associated with the disease.

Glaucoma is a progressive disease that is characterized by a specific pattern of damage to the optic nerve. Development of the disease can be attributed to many risk factors, including but not limited to high intraocular pressure (IOP), a family history of glaucoma, myopia, blood pressure, and diabetes. Age also is a critical factor (Hart, W. M., Jr., "The epidemiology of primary open-angle glaucoma and ocular hypertension", in R. Ritch, M. B. Shields, T. Krupin (eds): *The Glaucomas*. St. Louis, C. V. Mosby Co., pp 789–795 (1989)). The incidence of glaucoma increases approximately 10-fold between 50 and 70 years of age, ranging from about 0.2% of the population between the ages of 50 and 54 to 2.0% of the population aged 70–74. Also, primates with experimentally induced elevations of IOP show structure (Quigley, H. A. "Pathophysiology of the optic nerve in glaucoma". In: J. A. McAllister, R. P. Wilson, eds. *Glaucoma*. London: Butterworths; 30–53 (1986); Morrison, J. C., et al., "A rat model of chronic pressure-induced optic nerve damage". *Exp. Eye Res.* 64:85–96 (1997); Garcia-Valenzuela, E., et al., *Exp Eye Research.* 61:33–44 (1995); and John, S. W., et al., *Invest Ophthalmol Vis Sci.* 39:951–962 (1998)) and functional (Marx, M. S., et al., "The pattern ERG and VEP in glaucomatous optic nerve disease in the monkey and human", in R. Q. Cracco, I. Bodis-Wollner (eds): *Evoked Potentials*. New York, Alan R. Liss, Inc., pp 117–126 (1986); Marx., M. S., et al., *Doc Ophthalmol* 67:281–301 (1988(a))); Frishman, L. J., et al., *Invest Ophthalmol Vis Sci.* 37:125–141 (1996); and Harwerth, R. S., et al., *Invest Ophthalmol Vis Sci.* 40:2242–2250 (1999)) changes that are characteristic of humans with POAG, so implantation into primates for testing precedes implantation into humans.

While it is important to note that elevated IOP is neither synonymous with glaucoma nor a guaranteed predictor of disease, it remains the most important risk factor related to the disease. IPO can be associated with much of the development and progression of glaucoma damage that occurs through time. Patients with unilateral elevation of intraocular pressure that is secondary to other eye disorders often develop glaucoma.

In the normal eye (see FIG. 1), IOP is maintained at ~16 millimeters of Mercury (mmHg) by a balance in the production and drainage of aqueous humor from the anterior chambers of the eye. This clear, blood-derived fluid flows from the ciliary body through the pupil to the Schlemm's canal. The aqueous humor is then discharged through the venous system into the vascular sclera by passing through the trabecular meshwork, a sponge-like structure located in the anterior angle of the eye (Kobayashi, A. S., *Biomechanics of Medical Devices*, Marcel Dekker, Inc., New York, New York (1981)). If the balance of the rate of production of aqueous humor and the rate of discharge is changed, the IOP is affected.

A patient's IOP experiences cyclical change on a daily basis. Fluctuations in IOP around the average value occur due to every day activity and changes in environment. IOP can show many different patterns of changes throughout a day that include impulses, prolonged periods of high pressure, or periods of sub-normal pressure without the patient's knowledge (Puers, R., et al., *J. Micromech. Microeng.*, 10, pp. 124–129 (2000))

Measuring and monitoring of IOP is crucial for the diagnosis, treatment, management, and research of the disease. At the present time, the most common method for measuring a patient's IOP is a procedure called tonometry (Kobayashi, A. S., *Biomechanics of Medical Devices*, Marcel Dekker, Inc., New York, New York (1981)). While this method is considered to be very accurate for measuring IOP, there are several drawbacks. Only a single reading for the particular instant in time that the test is performed is possible. Also, a visit to a physician's office is generally required, thus individual measurements may be separated by long periods of time. Permanent damage to many parts of the eye, including the optic nerve and retina, can result within hours of the onset if the pressures are high enough. It is critical that IOP levels be monitored on a continuous basis so that pressure relieving drugs can be administered immediately after the onset of high pressures to minimize the risk of permanent damage.

An improved monitoring system would provide benefits in both clinical and research applications. Clinically, the primary targets for such a device would be patients with severe cases of glaucoma. From a research standpoint, there are many questions that are unanswered about the true effects of IOP. Doctors still do not know what the largest concern is: the peak pressure over 24 hours, the difference between the high and low pressure measurements for a day, the cumulative IOP over a period of time, or an average IOP level. It is quite possible that one or all of these factors play a significant role in the progression of glaucoma. In this regard, such a device could lead to an extensive gain in knowledge of glaucoma and better methods of treatment.

Sensors

Wireless capacitive pressure sensors are known and described in the Collins, IEEE Transactions on Bio-Medical Engineering, Vol. BME-14 No. 2 74–83 (April 1967); Rosengren, et al., J. Micromech. Microeng. 2 202–204 (1992); and Mokwa, et al., Proc. Microsystem Symposium Delft, 1–13 (1998)). Akar et al, Eurosensors XIV Aug. 27–30, 2000 describes such a device for general pressure measurement. This type of sensor are also described by Puers et al in J. Microeng 10 124–129 (2000). U.S. Pat. No. 5,005,577 to Frenkel describes a device which is implantable in the aqueous chamber of the eye. Jeffries et al, U.S. Pat. No. 6,193,656 also describes such a system. Waters et al, U.S. Pat. No. 4,922,913 describes a piezoelectric sensor. U.S. Pat. No. 6,213,943 to Abreu describes a radio wave transmitter connected to the eye. U.S. Pat. No. 6,312,380 to Hoek et al and U.S. Pat. No. 4,026,276 to Chubbuck describe capacitive sensors used in human systems.

There is a need for an improved method and system for monitoring fluid pressures in an animal, particularly in the eye of a mammal, such as a human.

OBJECTS

Therefore, it is an object of the present invention to provide an improved method and system for the detection of fluid pressure in general and in animals including humans, particularly in the eye, which provides the ability to have continuous monitoring.

These and other objects will become increasingly apparent by reference to the following description and drawings.

SUMMARY OF THE INVENTION

An implantable, biomedical pressure sensor to be fabricated utilizing Microelectrical Mechanical Systems (MEMS) technologies is described, as shown in FIG. 2. The sensor is one of three components in a pressure measuring system that are used to monitor intraocular pressure (IOP) on a continuous basis. The second component in the system is a data acquisition and processing (DAP) unit, while the third component is a central database that will be utilized for record keeping purposes.

The pressure sensor is implanted in the eye, for instance, and will provide wireless measurements of IOP. The device is small enough that the patient's vision and the function of the eye are not affected. The data acquisition unit services multiple purposes. The device generates a signal that is transmitted to the sensor through wireless telemetry, as well as acquires, processes, and temporarily stores the data that returns from the implanted sensor. The information is then uploaded to the central database so a complete time record of IOP measurements can be maintained.

The IOP sensor system employs the following:

1) Fully implantable, wireless, and passive (without batteries) sensor designed and built using MEMS technology;
2) Precision pressure measurement;
3) Continuous or scheduled measurement of IOP;
4) Variable data acquisition rate;
5) Alarm to alert patient of unsafe pressure levels;
6) Remote control of transmitter/receiver unit;
7) Portable transmitter/receiver unit with rechargeable batteries; and
8) Data storage for record keeping.

A cure for glaucoma is the ultimate advance, but accurate, remote monitoring of IOP has the potential to be as important to successful management of glaucoma in patients as the heart monitor is to heart patients. Saving people's vision is the ultimate goal.

The device, preferably made of silicon and glass, features an on-chip inductor and a parallel plate pressure-variable capacitor. The inductor is formed from a planar coil of gold, while the capacitor is comprised of a non-movable gold electrode housed inside the sensor and a thin flexible diaphragm exposed to the pressure exerted by the eye fluid. The sensor is a simple R-L-C resonant circuit. Pressure exerted on the diaphragm by the aqueous humor results in a micronscale deflection of the diaphragm causing a change in the capacitance of the sensor. The change in capacitance will in turn change the resonant frequency of the sensor. The planar inductor coil allows for wireless telemetry to a data acquisition and processing (DAP) unit by means of inductive coupling. Measuring the electrical characteristics of the DAP provides a measure of the resonant frequency of the sensor and thus a direct measure of the capacitance and the pressure in the eye.

Thus the present invention provides a method for determining fluid pressure within a living animal containing the fluid under pressure which comprises (a) providing a wireless capacitive MEMS chip sensor comprising an inductance coil (L) and spaced apart capacitor (C) plates as a inductive-capacitive (LC) circuit, optionally with an antenna externally of the sensor, with the fluid in the animal in pressure contact with one of the capacitive plates; (b) inducing a mutual inductance as an external signal into the sensor to produce a resonant frequency response as an internal signal from the sensor; and (c) determining the fluid pressure within the animal externally of the animal from the internal signal as a function of the resonant frequency response from the sensor resulting from a change in capacitance of the sensor due to a variation in the spacing of the plates produced by the fluid pressure. Preferably, an intermediate unit (IU) is provided outside of the eye to receive and then transmit the signals from the sensor to a remote data acquisition and processing unit (DAP) as shown in FIG. 29.

In a further embodiment, the plate in pressure contact with the fluid is a P++ doped silicon membrane.

In a further still embodiment, the coil is deposited on a substrate by sputtering and/or electroplating.

In a further still embodiment, the sensor has the antenna which receives the external signal and transmits back the internal signal for determining the fluid pressure.

In a further still embodiment, a temperature reading is determined by an element in the sensor. In a preferred embodiment, the element is a series resistance in the circuit wherein a response of the resistance changes as a function of temperature in the environment, which can be related to the pressure measurement. The environment is preferably a living animal, especially a human.

The present invention further provides a system for detecting increased fluid pressure in an animal which comprises (a) a sensor comprising a wireless MEMS chip capacitive sensor comprising an inductance coil (L) and spaced apart capacitor (C) plates as a inductive capacitive (LC) circuit, optionally with an antenna externally of the sensor, with the fluid in the animal with one of the capacitive plates; and (b) a mutual inductance producing device which measures a resonant frequency response of the sensor as an internal signal produced by the inductance device as an external signal relative to the animal, wherein the increased pressure of the fluid in the animal is detected over time as a result from a change in capacitance of the sensor due to a variation of the spacing of the plates produced by the fluid pressure; and (c) means for externally monitoring the fluid pressure in the animal as a function of the external signal. Preferably the means for monitoring includes memory means for storing a series of pressure determinations. Most preferably the memory means is a computer.

The present invention further provides a method for determining fluid pressure within an eyeball containing the fluid under pressure which comprises (a) providing a wireless capacitive MEMS chip sensor comprising an inductance coil (L) and spaced apart capacitor (C) plates as a inductive-capacitive (LC) circuit, optionally with an antenna external of the sensor, with the fluid of the eye in contact with one of the capacitive plates; (b) inducing a mutual inductance as an external signal into the sensor to produce a resonant frequency response as an internal signal from the sensor; and (c) determining the fluid pressure within the eyeball externally of the eyeball from the internal signal as a function of the resonant frequency response from the sensor resulting from a change in capacitance of the sensor due to a variation in the spacing of the plates produced by the fluid pressure in the eyeball.

In a further embodiment, the sensor is implanted in the vitriol chamber adjacent to the cornea of the eyeball. Also the sensor can be implanted in the aqueous chamber adjacent to the cornea of the eyeball.

In a further still embodiment, the pressure of the fluid is between about 10 and 20 mm of Hg (1333 to 2666 Pascal) for normal pressure of the fluid and between about 20 and 80 mm of Hg (2666 to 10,666 Pascal) for glaucoma.

The present invention further provides to a system for detecting increased fluid pressure and thus glaucoma of the eye which comprises (a) providing a wireless MEMS chip capacitive sensor comprising an inductance coil (L) and spaced apart capacitor (C) plates as a inductive capacitive (LC) circuit, optionally with an antenna externally of the sensor, with the fluid of the eye in contact with one of the capacitive plates; and (b) a mutual inductance producing device which measures a resonant frequency response of the sensor as an internal signal produced by the inductance device as an external signal relative to the eyeball, wherein the increased pressure of the fluid in the eyeball is detected results from a change in capacitance of the sensor due to a variation of the spacing of the plates produced by the fluid pressure in the eyeball; (c) means for externally monitoring the fluid pressure in the eyeball as a function of the external signal. Preferably the means for monitoring also includes an atmospheric pressure sensor, so that a pressure in the eyeball can be determined relative to the atmospheric pressure.

The present invention further provides a method for determining fluid pressure within an environment containing the fluid under pressure which comprises (a) providing a wireless capacitive MEMS chip sensor comprising an inductance coil (L) and spaced apart capacitor (C) plates as an inductive-capacitive (LC) circuit, optionally with an antenna externally of the sensor, with the fluid in the environment in pressure contact with one of the capacitive plates; (b) inducing a mutual inductance as an external signal into the sensor to produce a resonant frequency response as an internal signal from the sensor; and (c) determining the fluid pressure within the environment externally of the environment from the internal signal as a function of the resonant frequency response from the sensor resulting from a change in capacitance of the sensor due to a variation in the spacing of the plates produced by the fluid pressure in the environment.

The present invention further relates to a system for detecting increased fluid pressure in an environment which comprises (a) a MEMS chip sensor comprising a wireless capacitive sensor comprising an inductance coil (L) and spaced apart capacitor (C) plates as an inductive capacitive (LC) circuit, optionally with an antenna externally of the sensor, with the fluid in the environment in pressure contact with one of the capacitive plates; and (b) a mutual inductance producing device which measures a resonant frequency response of the sensor as an internal signal produced by the inductance device as an external signal relative to the environment, wherein the pressure of the fluid in the environment is detected over time as a result from a change in capacitance of the sensor due to a variation of the spacing of the plates produced by the fluid pressure; and (c) means for externally monitoring the fluid pressure in the environment as a function of the external signal. Preferably, an intermediate unit (IU) to receive and then transmit signals from the sensors to a remote data acquisition and processing (DAP) is provided adjacent to and outside of the fluid as shown in FIG. 29.

BRIEF DESCRIPTION OF DRAWINGS

In FIG. 26B a suture is used to tie the sensor to the wall of the eye. In FIG. 26A a suture is run vertical and the sensor is tied to this suture.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

Implant Options

Figure 1:
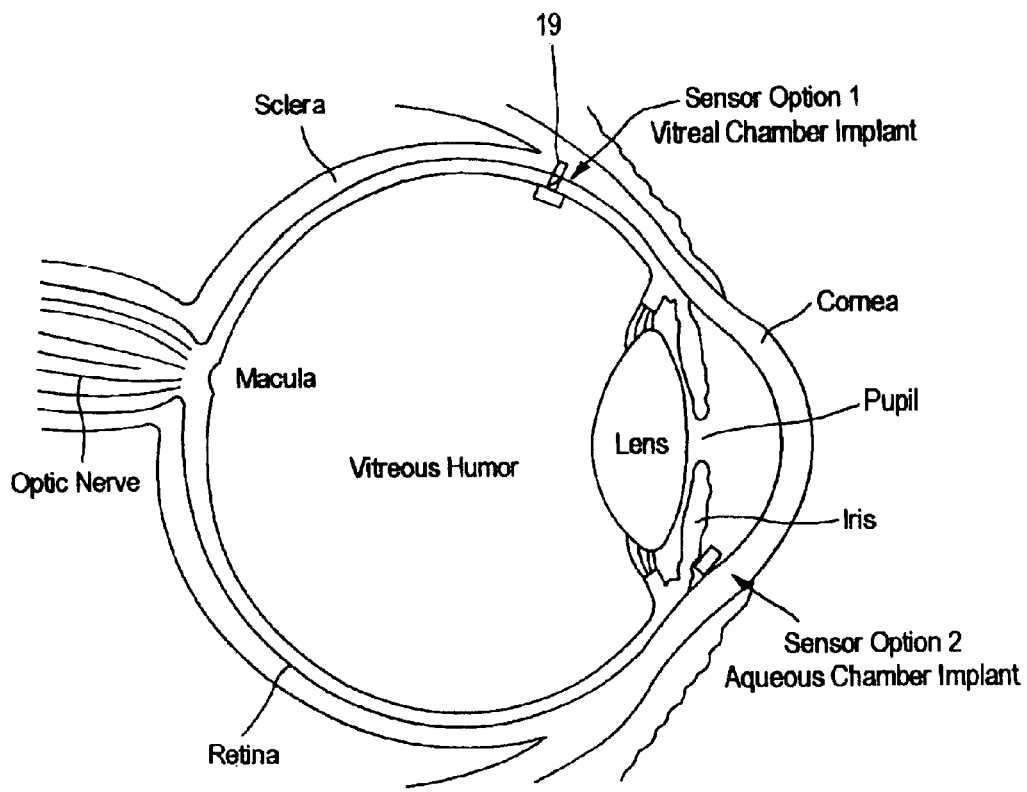
FIG. 1 is a schematic representation of the eye with the sensor 10 mounted in different positions in the eye.

There are two options for the location of the sensor implant. The device will be located either in the vitreal chamber or the anterior chamber of the eye, shown in FIG. 1. The implant will be attached to the wall of the eye or attached to a tether so that the device can easily be located if there is a need for it to be removed.

Operating Range

Normal levels of IOP are considered to be around 16 mmHg. Pressures over 22 mmHg are considered to be moderately high while pressures greater than 45–50 mmHg can be extremely dangerous. The pressure sensor has been designed to measure pressures in the range of 0 to 60 mmHg. It should be noted that all parameters were designed with the intent of manufacturing a device that can accurately produce full-scale measurements up to 60 mmHg. However, additional safety factors were included so that the device would remain functional even if the IOP should exceed the 60 mmHg limit of the design.

Overview

Figure 2:
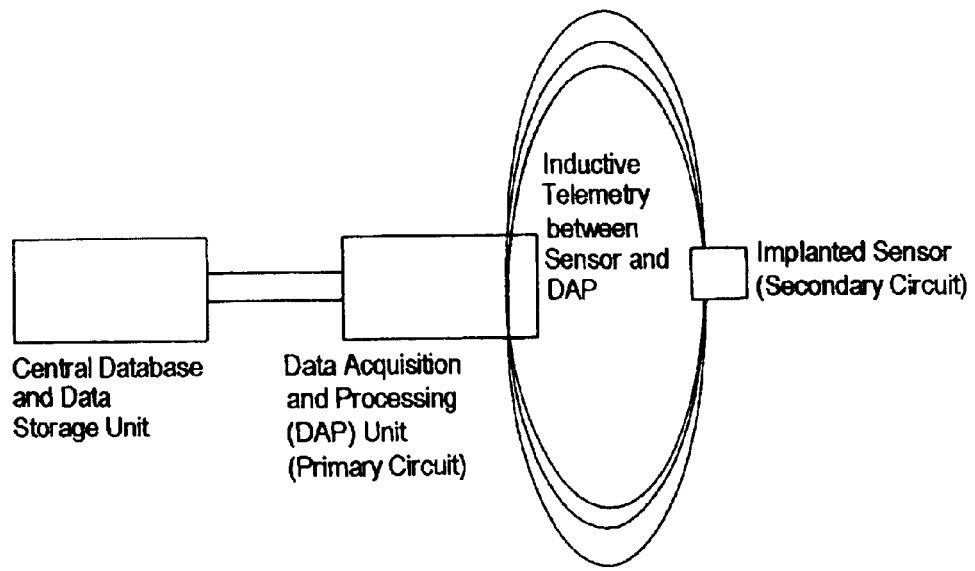
FIG. 2 is a schematic view of the system of the present invention.

The IOP monitoring system consists of three separate components as shown in FIG. 2: 1) a wireless, remote pressure sensor that is implanted inside the eye of the patient (secondary circuit), 2) a data acquisition and processing (DAP) unit located external to the body (primary circuit), and 3) a central data storage system that maintains a time record of the patient's IOP measurements.

The primary and secondary circuits communicate by means of inductive coupling. The primary circuit generates and transmits a time-wise periodic signal to the secondary circuit, or sensor. The excitation of the sensor feeds back to the primary circuit and changes the characteristics of the primary circuit. Measuring the frequency response to the periodic signal of the primary circuit provides information about the electronics, specifically the capacitance, of the sensor circuit, which is directly related to the pressure that is being exerted on the sensor.

Figure 3:
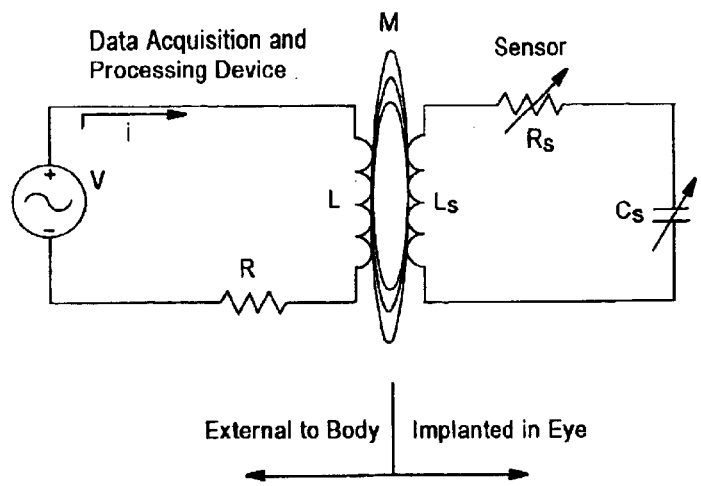
FIG. 3 is an equivalent RLC circuit diagram for the sensor of the present invention.

A schematic of the equivalent R-L-C circuit is shown in FIG. 3. The primary circuit has a current (i) and consists of a sinusoidal AC voltage source (V), an inductor (L), and a resistor (R). This resistor is referred to as the load resistor. The secondary circuit is an energy-conserving transducer that utilizes a pressure sensitive, variable capacitor ($C_s$), and an inductor ($L_s$). Any practical inductor must be wound with a wire that has some resistance, so it is impossible to have an inductor without some finite resistance. The resistance in the coil can be considered as a separate resistor $R_s$ in series with the inductor $L_s$ (The Bureau of Naval Personnel. "Basic Electricity." Dover Publications. New York, N.Y. (1969)).

Design Parameters

The design of the pressure sensor required optimization of the many linked parameters. The analysis and decision making process became complex as trade-offs in one area had to be made to improve another aspect of the design.

First, the pressure sensor is to be implanted in the human eye so overall size of the device is the most critical issue. The ophthalmologists associated with this project have constrained the largest dimension to not exceed about 3 millimeters. Anything larger than this could result in interference with normal vision or complicate the implantation process. Since the overall size of the pressure sensor must be less than 3 mm, this constraint is the most important parameter and will take precedence over all of the other factors in the design. Once it has been insured that the size constraint has been satisfied, maximizing the sensitivity of the device is the primary concern.

It is imperative that the sensor must be made of biocompatible materials. Most MEMS sensors utilize silicon and glass, which are biocompatible. Silicon is utilized because so much is known about it, and fabrication processes used to manufacture silicon devices are much more developed than for other materials. Glass is readily available and is very compatible with many fabrication processes. For these reasons, silicon and glass were chosen as the materials for all of the external structures.

The design also involves optimization of the physical dimensions for each of the components. The list of important parameters that were considered and optimized is provided in Table 1.

TABLE 1

List of Key Sensor Design parameters

| Capacitance | Capacitor Plate Side Length |
|---|---|
| Inductance | Capacitor Plate Separation |
| Frequency Range | Capacitance Range |
| Diaphragm Shape | Inductor Shape |
| Diaphragm Side Length | Number of Windings |
| Diaphragm Deflection | Inductor "Wire" Thickness |
| Diaphragm Thickness | Wire Height |
| Effects of Intrinsic Stress on Diaphragm Dynamics | Gap Between Windings |
| | Quality Factor and Resistance |

Conceptual Sensor Structure

Figure 4:
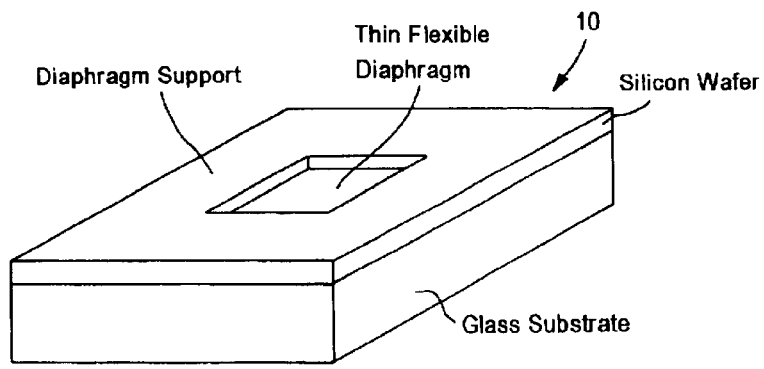
FIG. 4 is a perspective view of the sensor 10.

Preferably the base of the pressure sensor is a rigid structure, and the top surface is a flexible diaphragm (see FIG. 4). The sensor substrate and the diaphragm are electrostatically bonded together.

Figure 5:
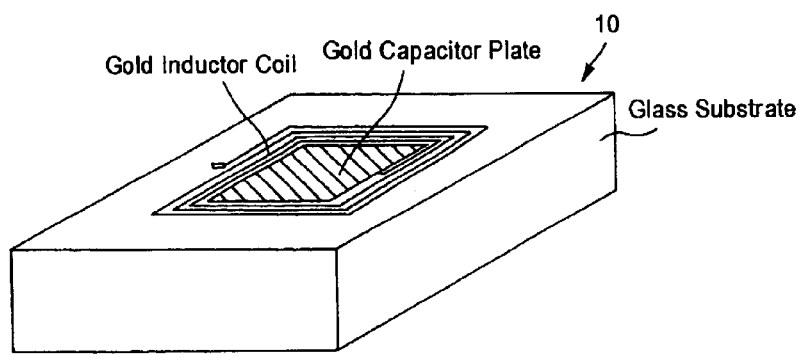
FIG. 5 is a perspective view of a sensor 10.

The substrate, or bottom wafer, is made of glass. This wafer houses the electrical components of the sensor. These components include a planar spiral inductor and a conductive electrode that are deposited on to the glass substrate. The basic layout is illustrated in FIG. 5.

Figure 6:
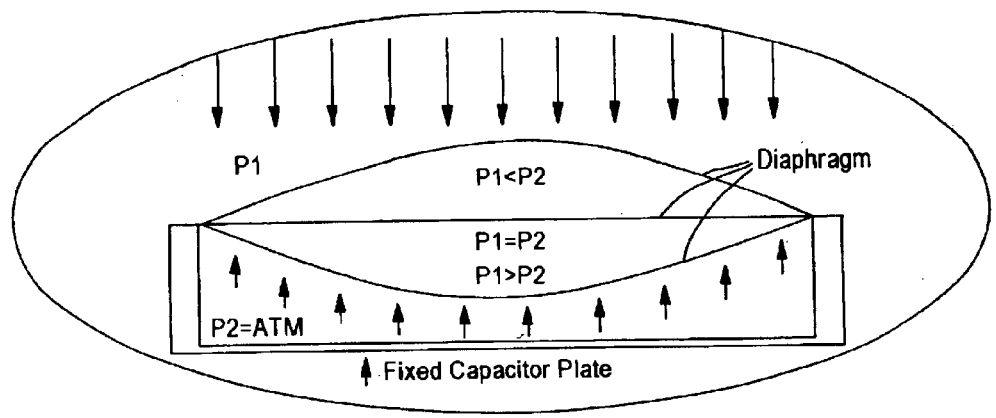
FIG. 6 is a side sectional view showing the operation of the sensor 10 which is shown in detail in FIG. 20.
Figure 7:
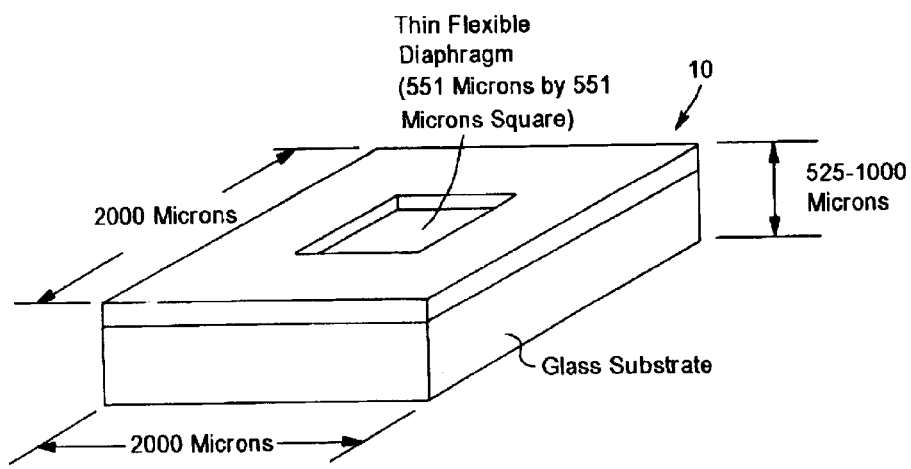
FIGS. 7, 8, 9, 10 and 11 show the dimensions of the components of the sensor.

The top wafer is made of (100) silicon. This wafer will be micro-machined and heavily doped with Boron to form a thin $p^{++}$ silicon diaphragm. The heavy doping makes the material conductive so the diaphragm can be used as a variable capacitor along with the electrode that is housed on the glass wafer. The pressure exerted on the sensor due to the fluid in the eye produces micron scale deflections of the diaphragm. The capacitance is a function of the electrode plate area and the gap height between the plates. The movement of the diaphragm results in a change in capacitance due to the change in the gap height, resulting in a variance of the resonant frequency of the sensor. The device is sealed with atmospheric pressure inside the capacitive chamber (a defined gap between the two wafers). The sensor system provides measurements relative to the pressure inside the cavity (FIG. 6).

The inductor is preferably a planar spiral that is made of gold electroplated on the glass substrate. A square spiral was chosen because of the ease of the layout and the symmetry. In general, planar inductors have a relatively low quality factor, or ability to absorb or emit energy, compared to other common forms of inductors, but the inductance value is well defined over a wide range and is tolerant to process variations (Mohan, S. S., et al., *IEEE J. Solid-State Circuits*, vol. 34, no., 10, pp. 1419–1424 (October 1999)). This is important because MEMS processes typically have a relatively high degree of variability due to the micron-scale features that are present. The quality factor is discussed in detail.

Design Dimensions

The dimensions of the device are shown in FIGS. 7, 8, 9, 10 and 11.

The device is a box with a width and length of 2000 microns. The glass wafers to be used for the substrate are typically available with a standard thickness of 500 microns. The total thickness of the device including the silicon is anywhere from about 525 to 1000 microns depending on the materials used.

Figure 8:
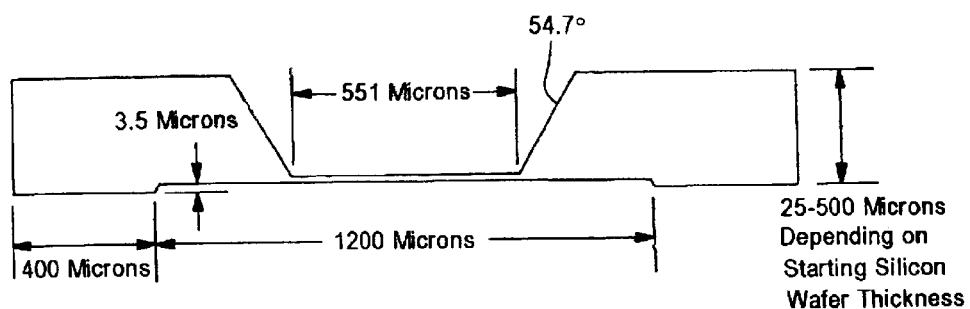

The diaphragm has a thickness of 4 microns (see FIG. 8 for dimension locations). The bottom of the silicon wafer is etched so that a 3.5 micron deep recess is created to define the capacitive gap. The 3.5 micron depth includes 2.0 microns to account for the electrode height above the surface of the glass wafer and 1.5 microns to account for the initial capacitive gap between the non-deflected diaphragm and the electrode. The side length of the recess is 1200 microns to ensure that the inductor coil does not touch the diaphragm. A 400 micron wide support structure surrounds the recess on the bottom of the wafer is used as the bonding surface between the silicon wafer and the glass substrate. The top of the silicon wafer is etched to form a 551 micron by 551 micron diaphragm. All of the etches results in a wide wall at an angle of 54.7° with the horizontal due to the crystalline structure of silicon.

Figure 9:
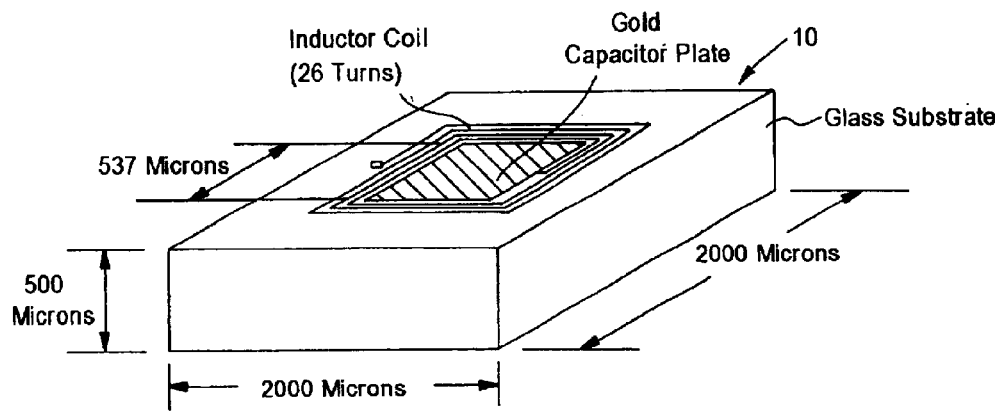
Figure 10:
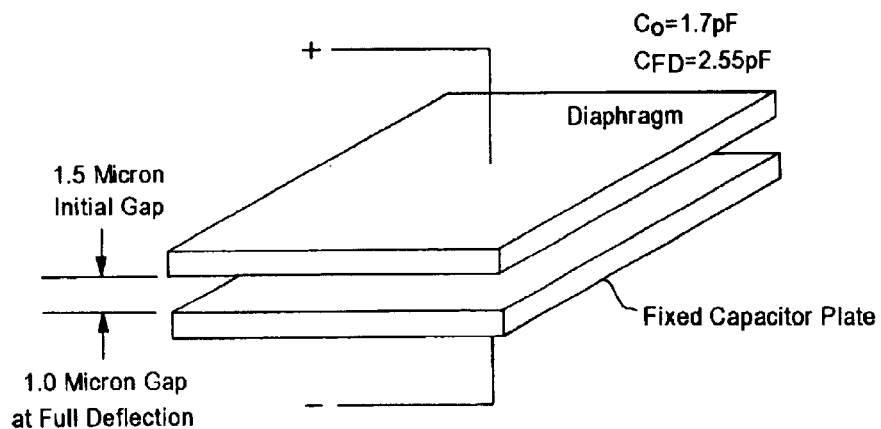

The capacitor plate is square with a side length of 537 microns (see FIGS. 9 and 10). The gold is etched so that the total thickness is 2.0 microns. This is so that the gap between the plate and the non-deflected diaphragm is 1.5 microns. The initial capacitance is preferably $C_o=1.7$ pF and the capacitance at full-scale deflection is preferably $C_{FS}=2.55$ pF.

Figure 11:
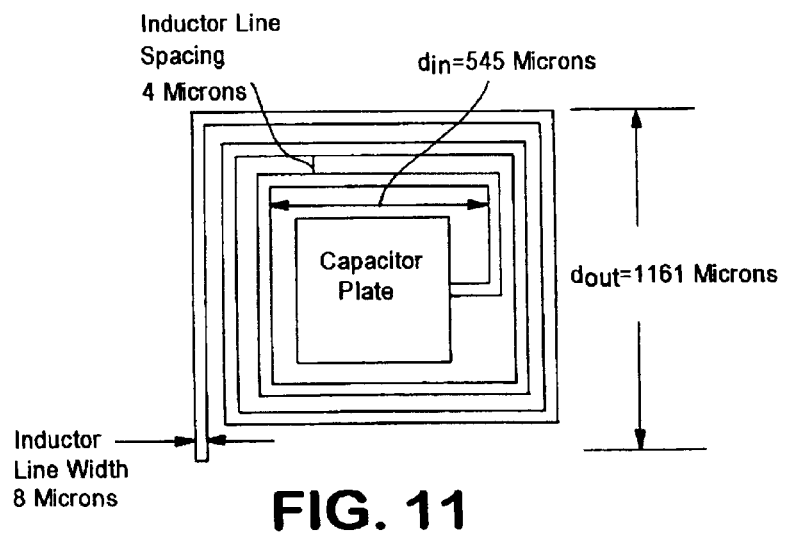

The inductor consists of 26 turns of gold wire. The wire is preferably electroplated on to the glass substrate. The physical dimensions are shown in FIG. 11. The inside diameter of the coil ($d_{IN}$) will be 545 microns with a 4 micron gap (s) between each turn. The wire has a line width (w) of 8 microns and line height ($t_w$) of 9 microns. As a result of these dimensions, the outer diameter ($d_{OUT}$) is 1161 microns, and the final inductance of the device is then 800.2 nH.

Due to the inductance value and capacitance range of the device, the size of the resonant frequency range of the device is 25.04 MHz with a resonant frequency of 136.46 MHz corresponding to 0 mmHg pressure difference across the diaphragm, and 111.43 MHz corresponding to 60 mmHg.

Fabrication Overview

A fabrication "recipe" for the sensor is presented in the following sections. The illustrations presented in the text show the cross-section of a single device so that each step can be clearly understood and visualized. However, in the actual fabrication of the devices, many individual devices are made from a single wafer, and the entire wafer will be fabricated at once. Hundreds of devices can be completed simultaneously.

Fabrication of the Glass Wafer

A layer of photoresist (PR) is spun and baked on the wafer.

Figure 12A:
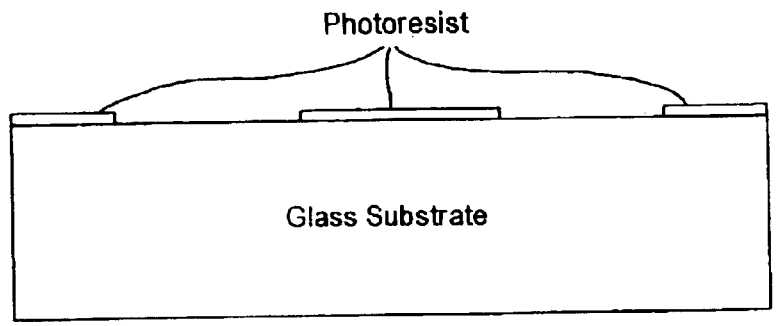
FIG. 12A is a side view showing the photoresist for etching the coil recess.

A lithography process is then required to define the coil recess. During lithography, a mask is used to define the patterns for the features on the substrate (see FIG. 12A). The wafer and mask are then exposed to a UV source. The photoresist (PR) is developed and a pattern is left on the glass wafer that is used as a mask for etching. This entire process, including spinning the PR, is referred to as the lithography process for the remainder of this description.

Figure 12B:
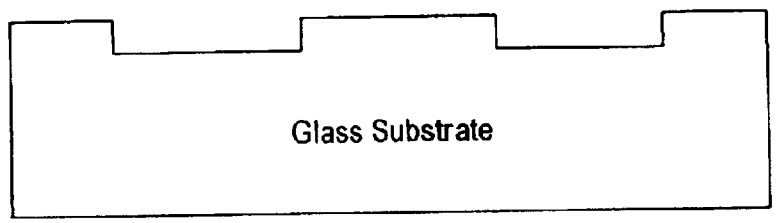
FIG. 12B shows the recess.

After a recess of about 10 microns is etched into the glass substrate, the PR is removed and the structure seen in FIG. 12B remain.

Next, a lithography process is required to define the capacitor plate, the electrical contacts that will be used to connect the upper and lower wafers, and the inductor coils.

A thin seed layer (Ti/Au) is deposited on the substrate. This seed layer allows thicker layers of gold to be deposited that will become the capacitor plate and the inductor coils. The gold is deposited by electroplating. The electroplating is continued until the inductor coils are at a thickness of 7 to 9 microns tall. An additional etch step may be desired to make the capacitor plate thinner.

Figure 13:
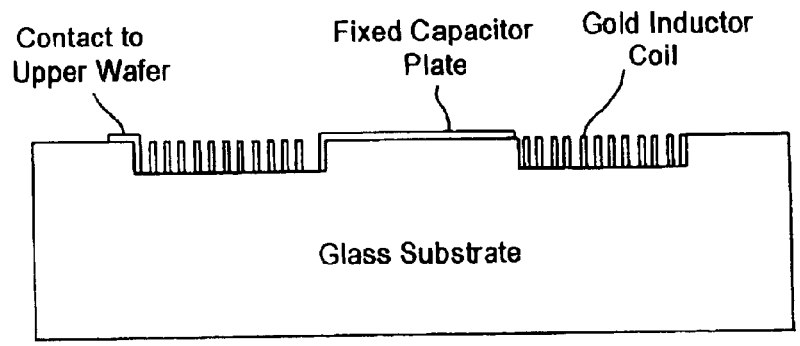
FIG. 13 is a side view showing the glass wafer with a Ti/Au layer deposited on the glass.

After the PR has been removed, the glass wafer is complete. The completed glass wafer with all of the on chip electronics can be seen in FIG. 13.

Fabrication of the Silicon Wafer

Figure 14:
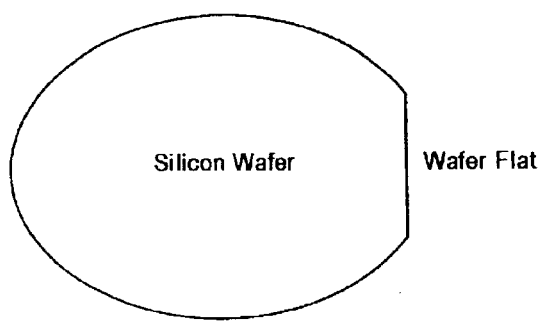
FIG. 14 is a plan view showing the silicon wafer for the sensor 10 with a (100) orientation.

The second wafer to be processed is a (100) silicon wafer (see FIG. 14). The (100) wafer is a thin, circular disk of silicon that has a (100) crystallographic plane as its top surface. A "flat" is located on the edge of the disk that corresponds to the (100) plane. This means that the <100> direction is normal to the top surface and the <100> direction is normal to the flat.

To complete the fabrication, both sides of the silicon wafer must be processed. A thin layer of $Si_3N_4$ is deposited on the silicon substrate.

Figure 15:
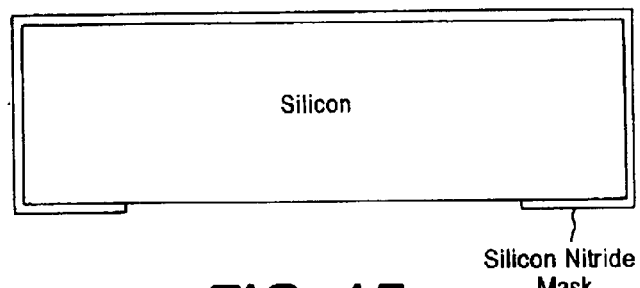
FIG. 15 is a side view showing a silicon wafer with a $Si_3N_4$ mask for defining the capacitive cavity.

A lithography process is then performed to etch the nitride so the capacitive cavity will be defined. The silicon wafer and mask are shown in FIG. 15.

Figure 16:
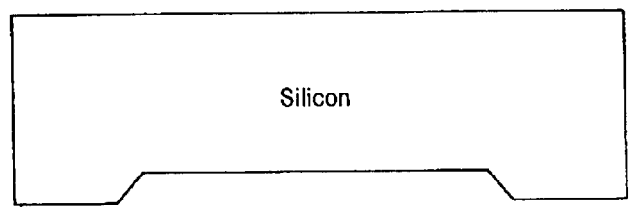
FIG. 16 is a side view showing the cavity which is etched into the structure of FIG. 15.

This cavity is etched to a depth of 3.5 microns seen in FIG. 16. This accounts for the 2 micron thick capacitor plate and the 1.5 microns capacitive gap. The silicon etches at an angle of 54.7° because of the crystallographic structure of the silicon atom. The (100) and (111) planes intersect at an angle of 54.7° within the crystal lattice. KOH is used as the etchant for this procedure. KOH has a selectivity ratio of 400:1 for (100) over the (111) planes. This means that 400 microns in the <100> direction will etch for every 1 micron that is etched in the <111> direction. The nitride mask is then etched away.

Figure 17:
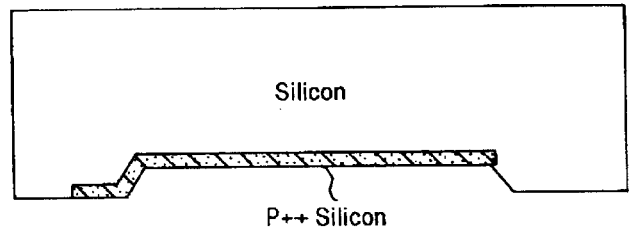
FIG. 17 is a side view showing a $P^{++}$ silicon in the capacitive cavity of FIG. 16.

A lithography process is performed to define the diaphragm area and electrical contacts. The photoresist is used as a mask for a diffusion step. A process called Ion Implantation is used to introduce Boron to the surface of the membrane. A high-energy beam of Boron ions is directed at the silicon wafer and Boron is literally forced in to the surface of the silicon. The substrate is then annealed in an oven at a temperature in the range of 500–900° C. This annealing step allows the Boron ions to diffuse further in to the silicon to a depth of 4 microns to define the diaphragm thickness. The diffusion depth is a function of the intensity of the energy beam, temperature, and time. This creates a region of $p^{++}$ silicon seen in FIG. 17.

Figure 18A:
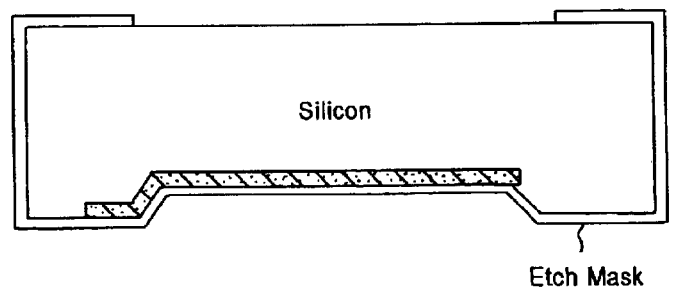
FIG. 18A is a side view showing the silicon wafer with the PR mask to define the diaphragm.

The Boron diffusion serves two purposes. First, a concentration dependent etch-stop is formed in the silicon wafer. $P^{++}$ silicon will not etch in common etchants such as KOH and Ethylene Diamine Pyrocatechol (EDP) as long as the concentration is high enough. Boron must have a concentration greater than $10^{20}$ cm$^{-3}$ or $5 \times 10^{19}$ cm$^{-3}$ to be an etch stop in KOH or EDP respectively. Concentration dependent etch stops allows for very accurate etching so the diaphragm thickness can be controlled to within about 0.1 microns. This is particularly important for controlling the dynamic response of the diaphragm to pressure. The second purpose of the diffusion step is that $p^{++}$ silicon is a conductive material where non-doped silicon is not conductive. This makes it possible for the diaphragm to be an electrode in the variable capacitor. A lithography process is then performed on the top of the wafer to define the diaphragm window, and etching is performed, as shown in FIG. 18A.

Figure 18B:
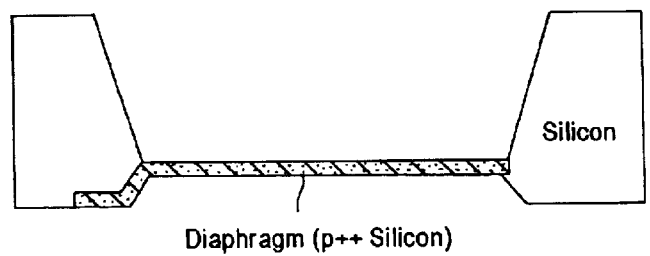
FIG. 18B is a side view showing the device with the completed silicon wafer and the $P^{++}$ silicon diaphragm.

Again, the silicon will etch at an angle of 54.7° because of the crystallographic structure of the silicon atom. The etching will continue until the boundary of the $p^{++}$ silicon has been reached. The shape of the silicon wafer can be seen in FIG. 18B after the completion of the etch step removal of the mask.

Electrostatic Bonding of Wafers

Figure 19:
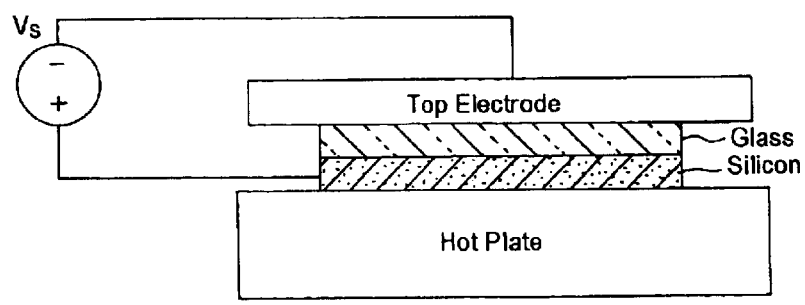
FIG. 19 is a schematic view showing the process for the assembly of the two wafers.
Figure 20:
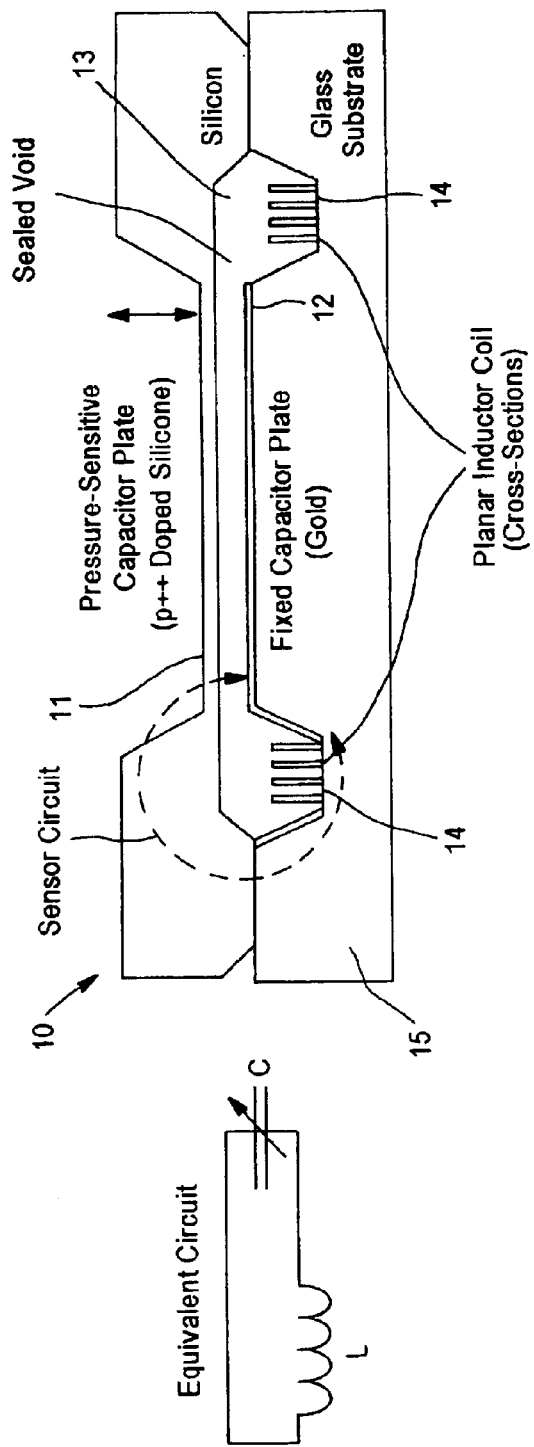
FIG. 20 is a schematic view of the sensor 10 which is placed in contact with fluid in the eye. The size is 1 to 3 $mm^2$ and the device is preferably round.
Figure 21:
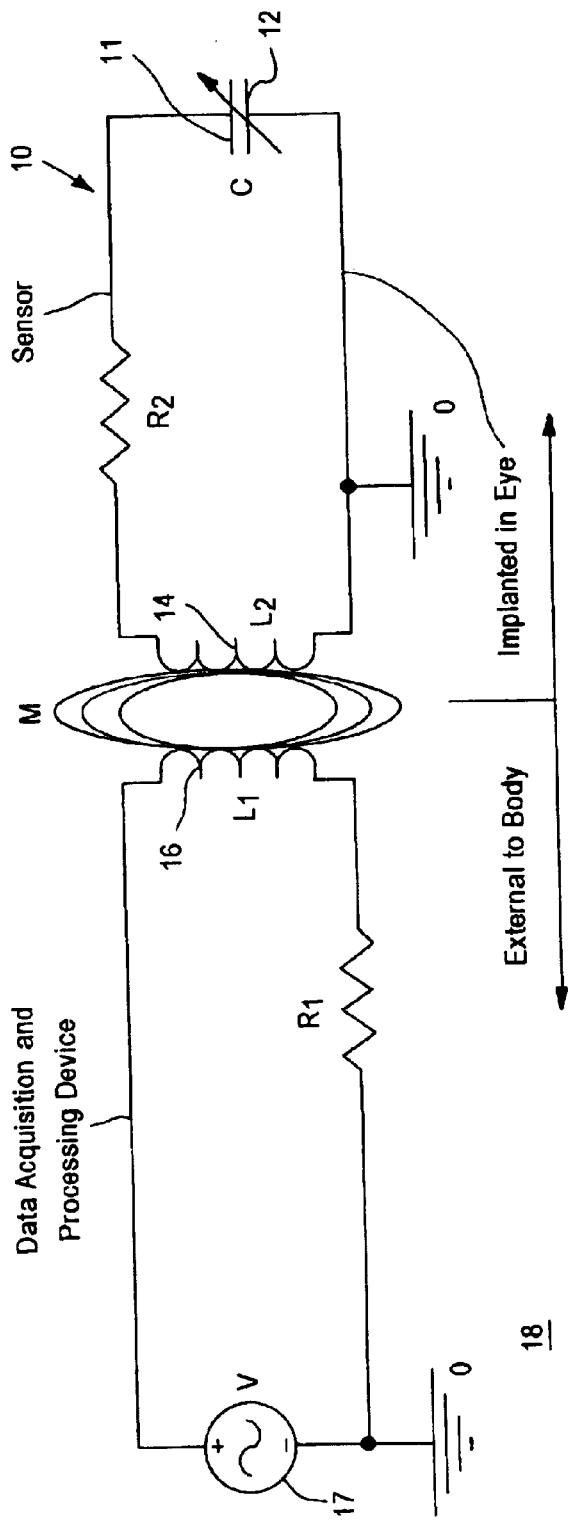
FIG. 21 is a schematic diagram of equivalent circuit of the sensor 10 in FIG. 20.
Figure 22:
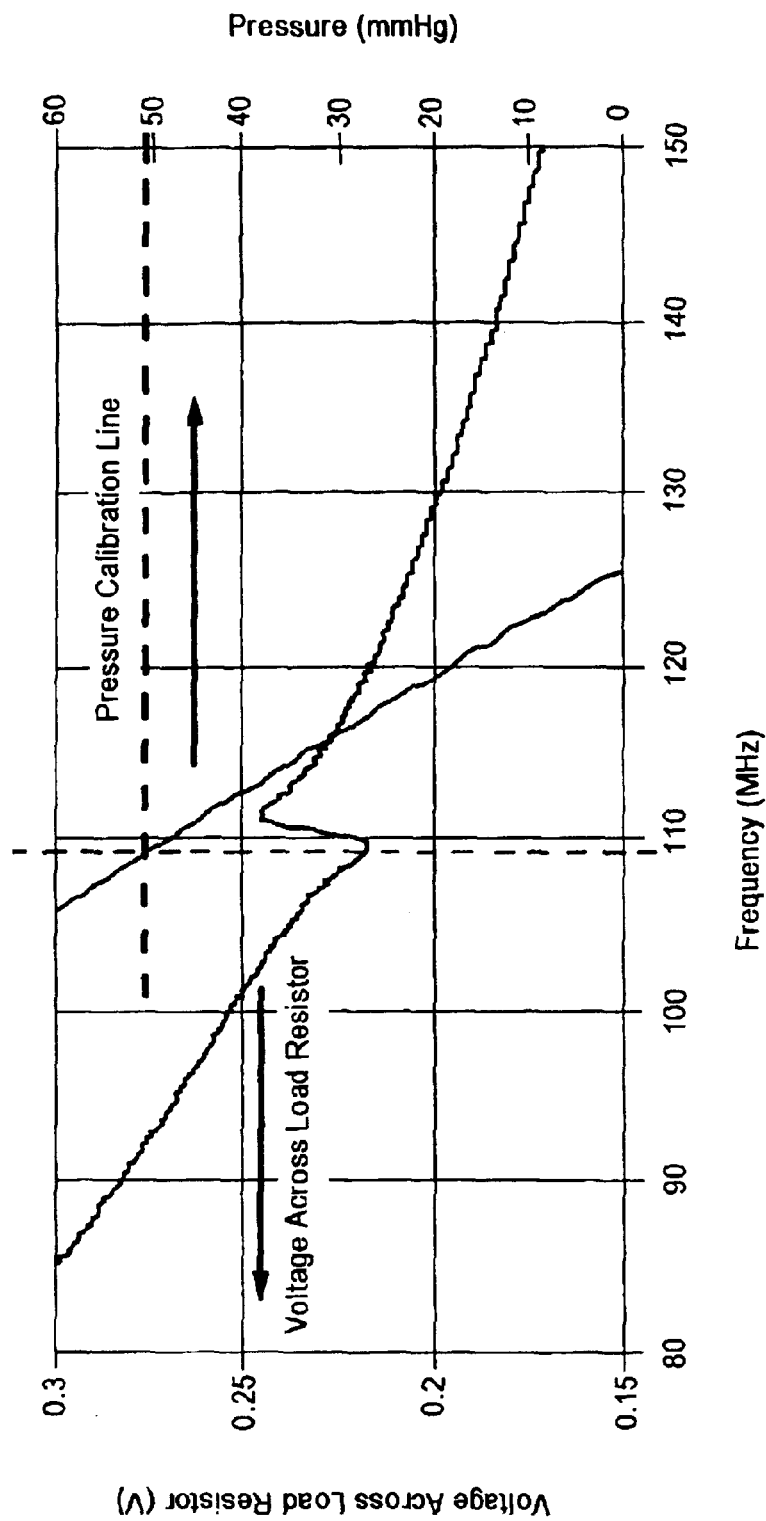
FIGS. 22, 23 and 24 are graphs showing expected response of the sensor 10 and the resonant frequency.
Figure 23:
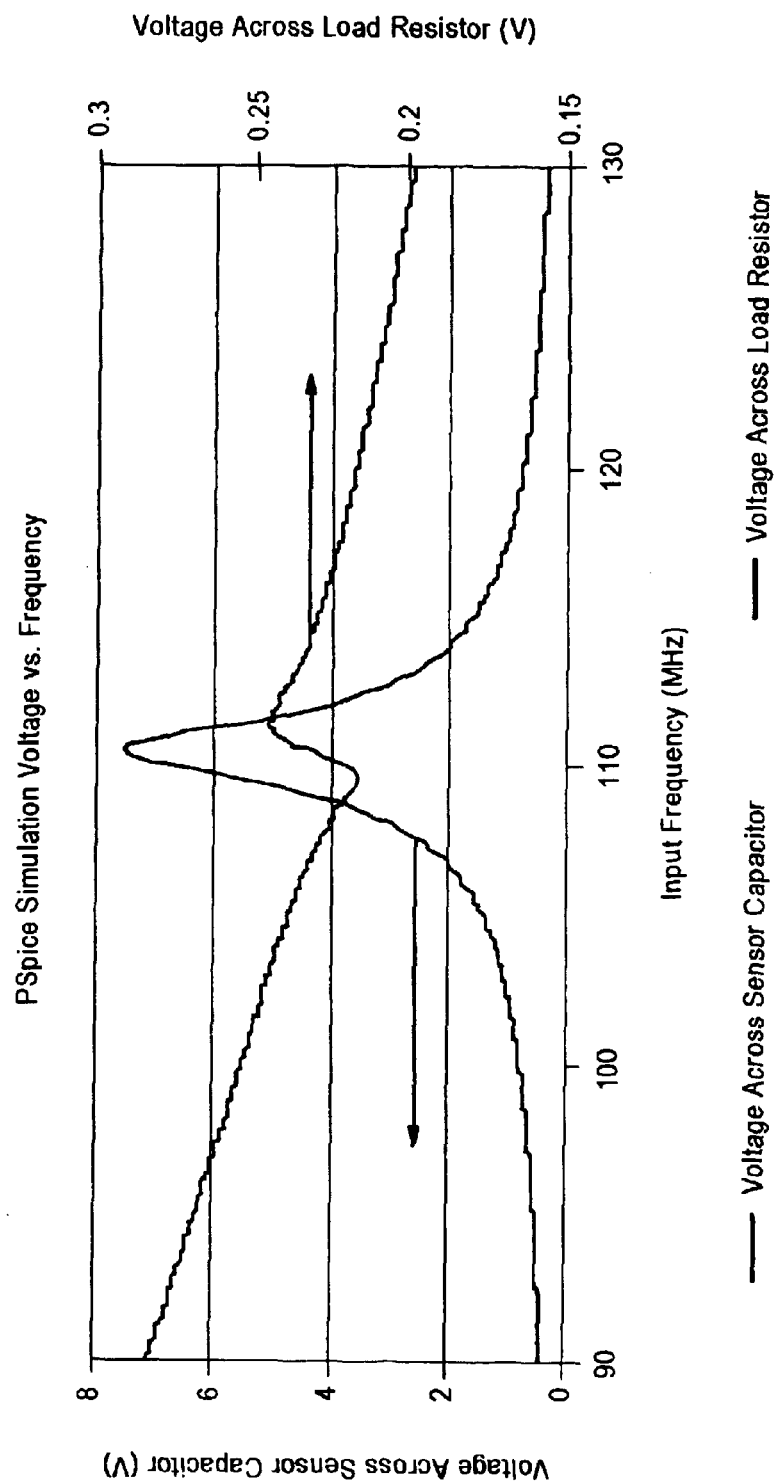
Figure 24A:
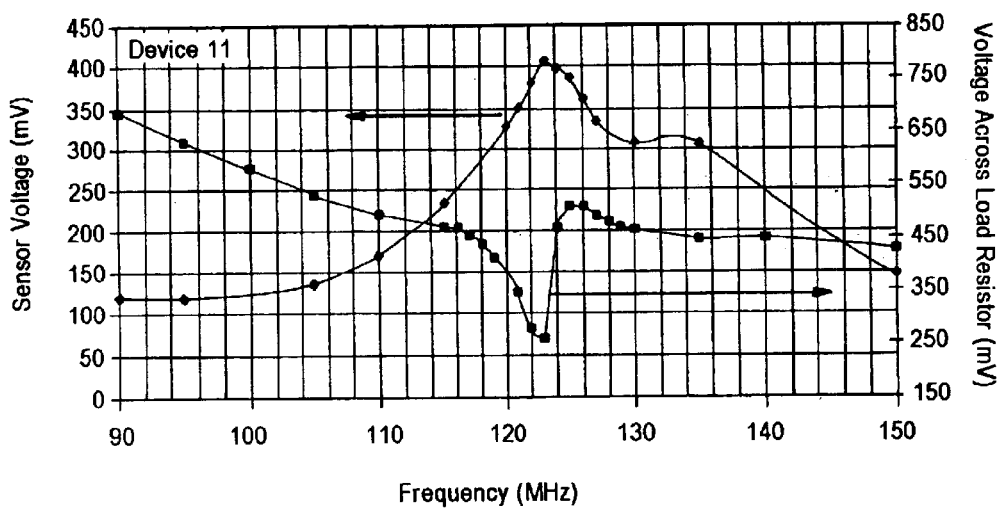
Figure 24B:
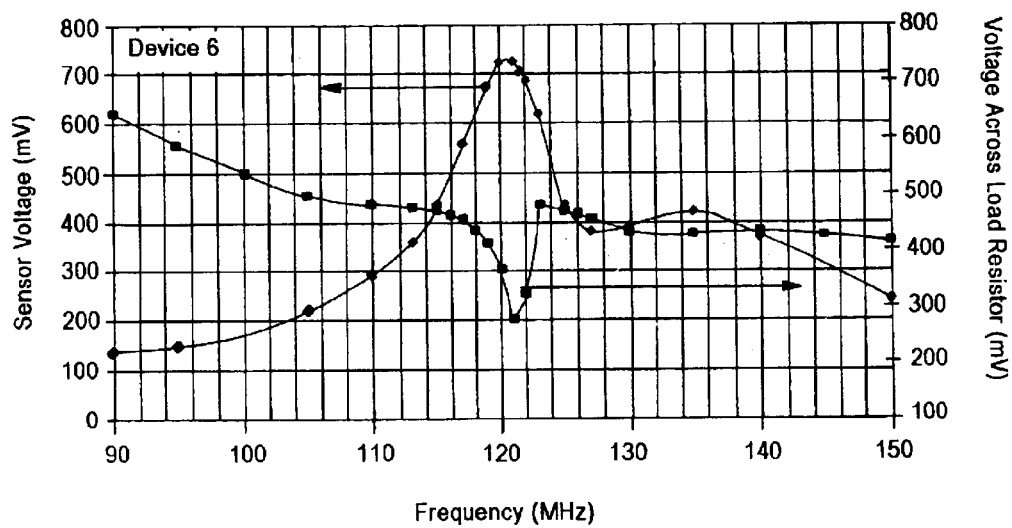
Figure 24C:
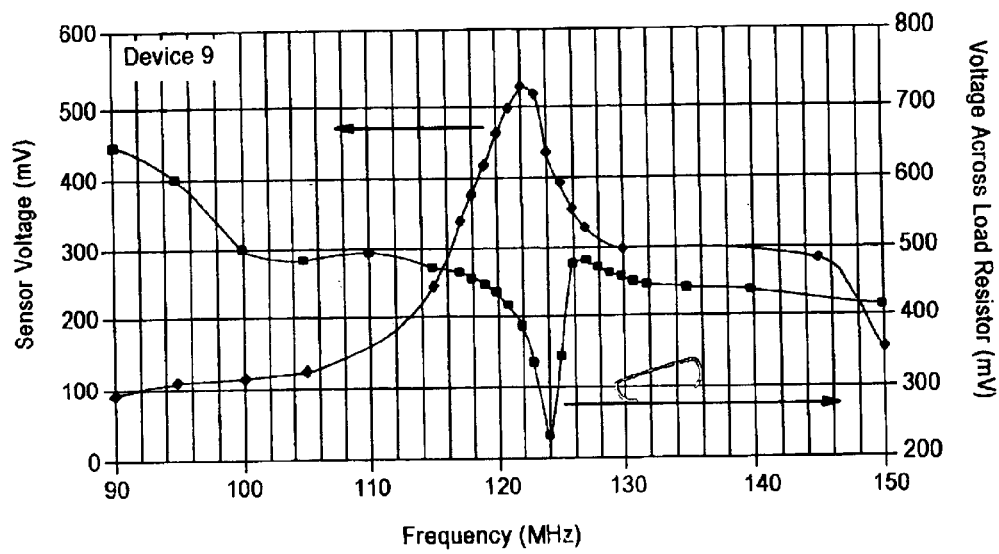
Figure 25:
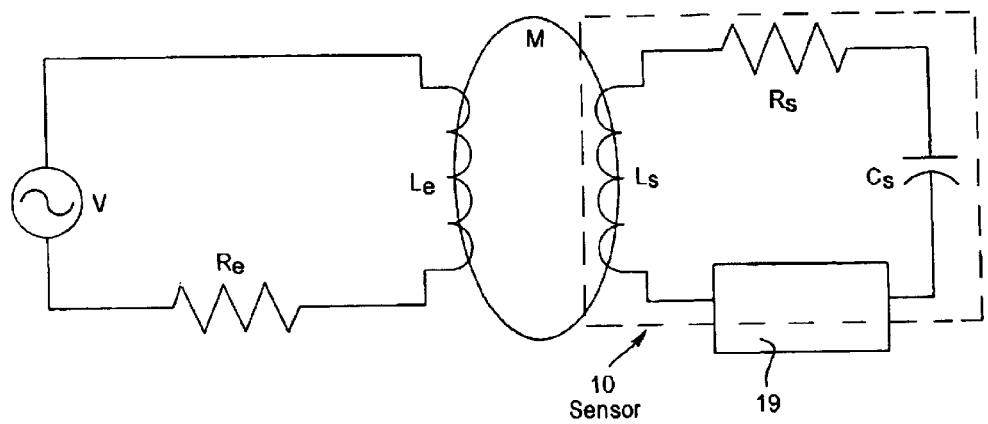
FIG. 25 is a schematic view of a circuit diagram for the eye pressure sensor wherein $L_e$: Inductor in external readout circuit; $R_e$: Resistor in external readout circuit; $L_s$: Inductor in implanted sensor; $C_s$: Pressure dependent capacitor in implanted sensor; $R_s$: Parasitic resistance in implanted sensor; M: Mutual inductance; and A: Antenna.

The two wafers are brought together by an electrostatic bond. The setup can be seen in FIG. 19. The top of the glass wafer is brought in to contact with the bottom of the silicon wafer and sandwiched between two electrodes. The positive electrode is in contact with the silicon while the negative electrode is in contact with the glass. The sandwich is raised to a temperature of about 400° C. and a DC voltage of about 1000 Volts is applied. The voltage causes mobile sodium ions to pull toward the negative electrode, which leaves oxygen at the interface between the two wafers. The electrostatic voltage also pulls the two wafers very close. The oxygen ions in the glass bond to the Si atoms at the surface and a very strong $SiO_2$ bond is created.

There is a need to quantify the actual pressure inside the sensor. This pressure is used as a reference and the sensor measures only the differential pressure. Theoretically, since the device is sealed in ambient conditions, the pressure in the cavity should be equal to 1 ATM. Initially, air was chosen as the gas to be present in the device. However, during the electrostatic bond a quantity of the oxygen would be consumed to form $SiO_2$ bonds on the surface of the diaphragm. This will result in lowering the pressure enclosed in the cavity.

There is a sufficient amount of silicon atoms at the surface of the capacitive cavity to react with all of the oxygen present so it stands to reason that the pressure enclosed inside the cavity would actually be reduced by 0.2 ATM (Goustouridis, D., et al., *Sensors and Actuators* A 68, pp. 269–274 (1998)). The actual volume enclosed in the cavity would only be about 0.8 ATM (608 mmHg) as opposed to the theoretical pressure of 1 ATM (760 mmHg).

Bonding the wafers in a nitrogen ambient instead of air eliminates the reaction.

Another factor to consider is the temperature dependence of the sensor. Since the sensor is sealed in air instead of vacuum the sensor becomes dependent on temperature due to the expansion of the gas trapped inside the cavity (Goustouridis, D., et al., *Sensor and Actuators*, A 68, pp. 269–274 (1998)). Fortunately, the temperature in the eye is maintained nearly constant by the body so the temperature will not fluctuate more than a few degrees. However, the electrostatic bond that seals the device occurs at a temperature of about 400° C. The gas will compress slightly as the temperature is reduced and the pressure inside the cavity will be lower than 1 ATM (Akar, O., et al., *Sensors and Actuators* A 95, pp. 29–38 (2001)). Testing will provide the actual pressure inside the cavity. It is possible to seal the device at an elevated pressure, so possibly the device could be sealed initially with greater than 1 ATM of pressure so that the final pressure after cooling is 1 ATM.

The present invention provides a design of an implantable, biomedical pressure sensor to be fabricated by standard Microelectrical Mechanical Systems (MEMS) technologies. The objective of this invention is to design and develop a micro-sensor intraocular pressure measuring system that can be implanted in the patient's eye for the purpose of glaucoma treatment/management.

As can be seen from FIGS. 20, 21, 22, 23, 24, 25 and 26, the system easily enables the detection of the pressure as a function of the resonant frequency response of the sensor 10. The sensor 10 includes a membrane capacitive plate 11, a fixed capacitive plate 12 with a void 13 between the plates 11 and 12. A wireless, electro-deposited coil 14 is provided on a non-conductive substrate 15 below the plates 11 and 12.

Figure 26A:
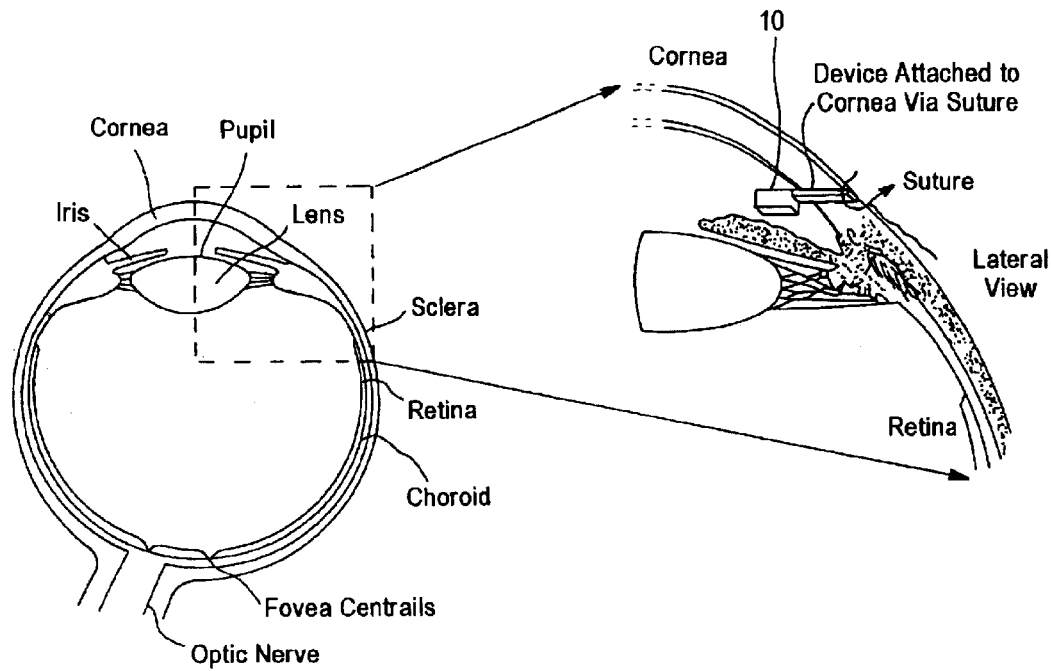
FIGS. 26A and 26B are schematic views showing two options for the implantation and suturing of the eye pressure sensor into the eye. Two issues for the implantation are the holding of the sensor with a suture so that it does not move freely inside the eye and the ability to easily retrieve the sensor at a later date. Two techniques for holding the sensor in the eye are shown in FIGS. 26A and 26B.
Figure 26B:
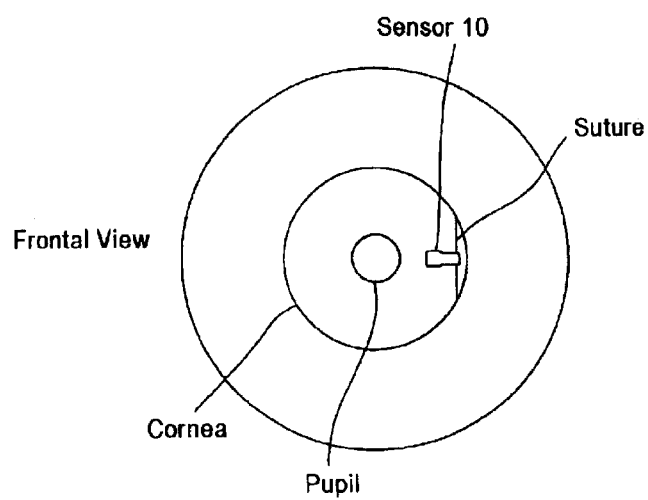

A second coil 16 in external device 18 is used to provide a variable inductance field from coil 16 to coil 14 by means of a variable voltage source 17. The device 18 including coil 16 also measures the resonant frequency of the sensor 10 in response to the inductance from coil 16. The sensor 10 fits in the eye as shown in FIGS. 26A and 26B. The eye pressure sensor 10 is preferably part of a system which transfers the data from the patient or animal to the doctor or veterinarian.

A cylindrical configuration of the sensor 10 is more sensitive than a square sensor structure. The cylindrical structure has a greater deflection and a larger area of greater deflection than a square structure of equal area. The advantage is a greater sensitivity and accuracy of the cylindrical sensor.

An improvement in the present invention is an antenna 19 (FIG. 25) attached to the sensor 10 that serves to improve its operation. The antenna 19 can also be used to mount or tie the sensor 10 in a specific region of the eye or animal for later retrieval. FIGS. 27A, 27B, 27C, 28A, 28B and 28C show numerous variations of the sensor.

The preferred design has the following characteristics shown in Table 2.

TABLE 2

Summary of Inductor Design

| | |
|---|---|
| Spiral Shape | Square |
| Turns | 26 |

TABLE 2-continued

Summary of Inductor Design

| | | |
|---|---|---|
| Inductance | 800.2 | nH |
| Line Thickness | 9 | microns |
| Line Width | 8 | microns |
| Turn Spacing | 4 | microns |
| Inner Diameter | 545 | microns |
| outer Diameter | 1161 | microns |
| Resonant Frequency At 0 mmHg | 136.46 | MHz |
| Resonant Frequency At 60 mmHg | 111.42 | MHz |

Figure 27A:
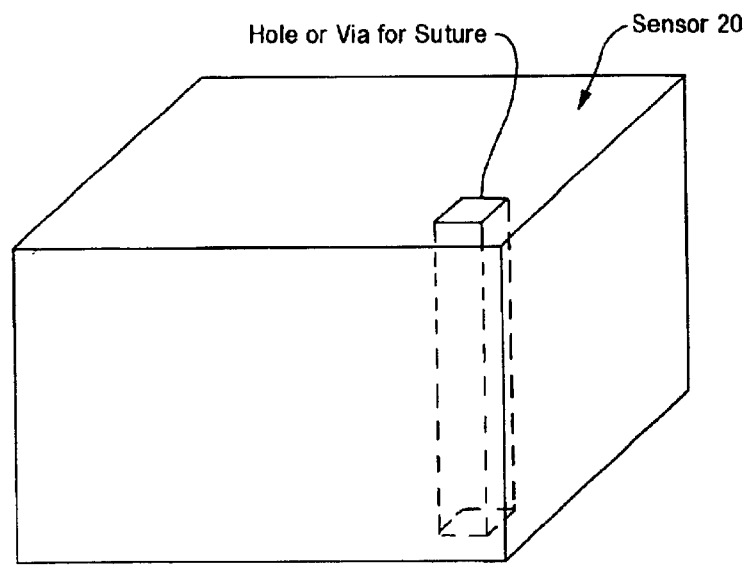
FIGS. 27A, 27B and 27C are perspective views showing variations for placing a hole or via through the sensors 20, 30 or 40 so that it can be held by the suture.
Figure 27B:
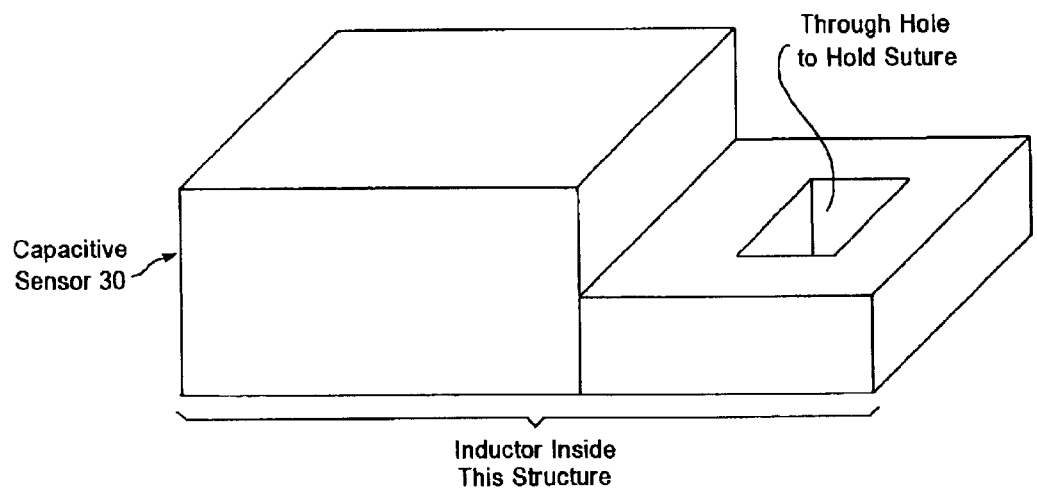
Figure 27C:
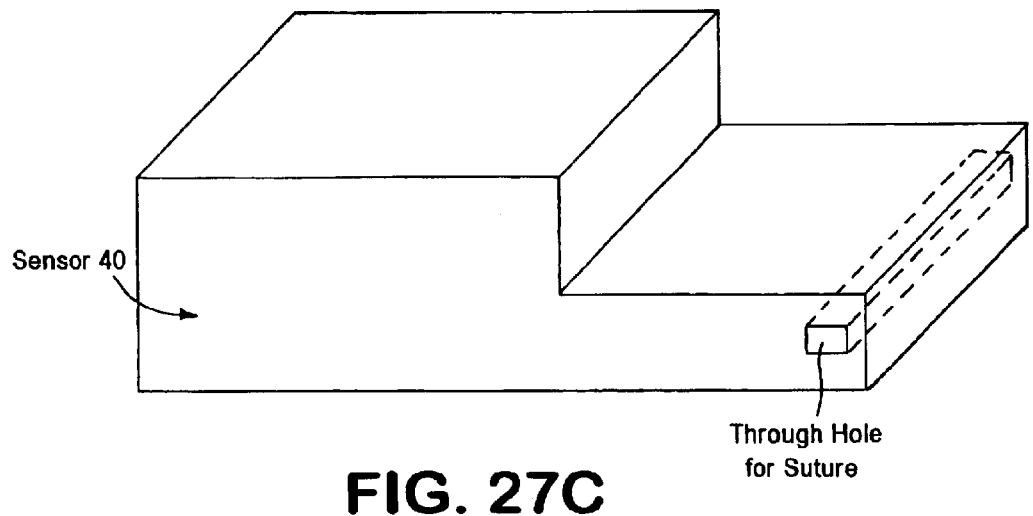

FIG. 27A shows the suture hole going through the implanted sensor 20 at a position that would not interfere with the inductor or capacitor located inside the sensor. FIG. 27B shows the sensor 30 built with an added tab structure, which has a hole in it for the suture to pass through. FIG. 27C shows a hole in the sensor 40 for the suture passing through the tab in the long direction. This facilitates using the suture to orientate the device in the eye so that good coupling is obtained between the sensor coil and the external coil. The orientation would be accomplished using the vertical suture line as shown in FIG. 26B.

Figure 28A:
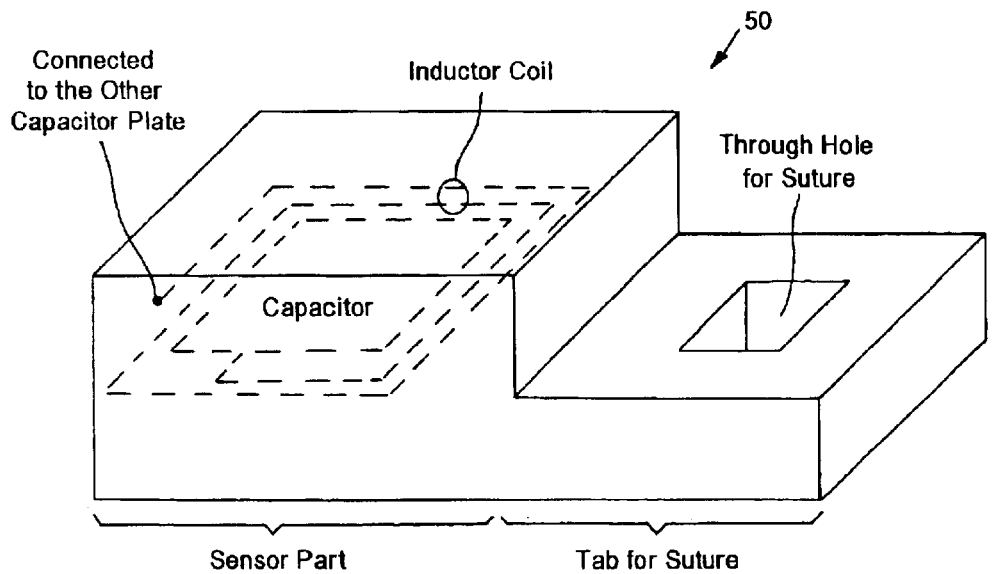
FIGS. 28A, 28B and 28C are perspective views showing variations for the placement of the inductor coil in sensor 50, 60 or 70.
Figure 28B:
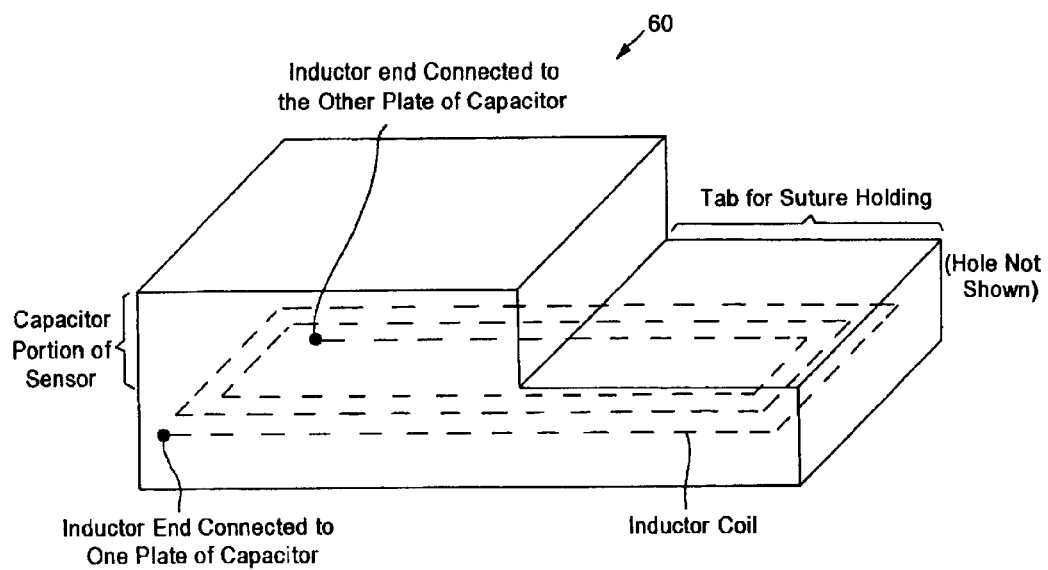
Figure 28C:
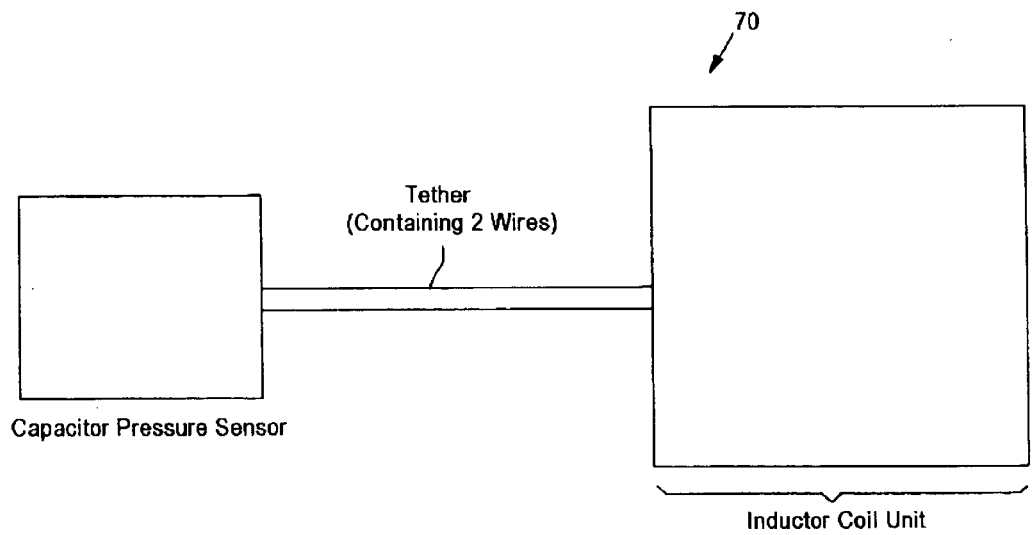

FIG. 28A has the inductor coil located so that it surrounds the capacitor. FIG. 28B has the inductor coil in the sensor 60 occupying both the capacitive sensor portion of the sensor and the holding tab portion of the sensor. The larger area of the coil will allow an increase in the distance that the external sensor can be placed away from the implanted sensor coil. The inductor coil could be located inside the sensor structure or built on the bottom of the sensor structure. FIG. 28C has the inductor coil and capacitor portions of the sensor 70 as distinct units that are tethered together via a tether connector containing two wires. With this unit the inductor can be implanted near the surface of the body (the eye for example) and the capacitor sensor can be implanted further into the body. The inductor portion of this sensor could have a hole for suture holding located in it as shown in FIG. 28B.

One of the concerns of the inductive telemetry system is the need to have the external inductor coil located "reasonably close" to the implanted sensor. "Reasonably close" here is a distance of less than a few centimeters (3–5 cm). The size of the data acquisition and processing unit (DAP) shown in FIG. 2 may be too large for some applications. In particular, it may not permit the convenient use of the IOP sensor system for humans and it may prevent its use in some animals.

Figure 29:
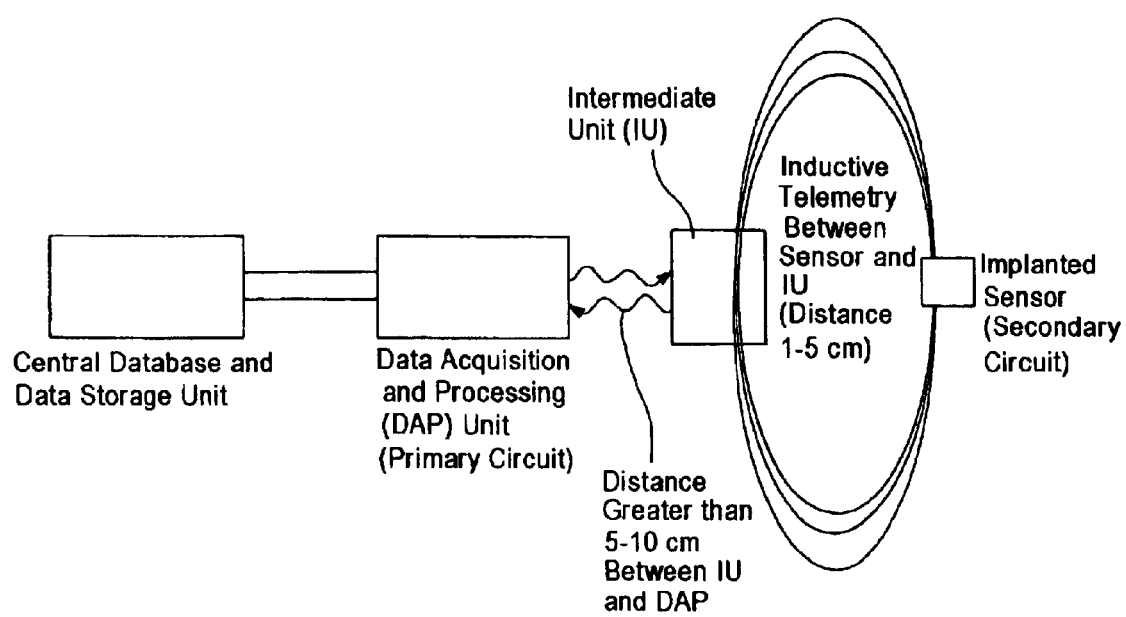
FIG. 29 is a schematic representation of the system of the present invention with an intermediate unit (IU) for receiving and then transmitting a signal from the sensor to a data acquisition and processing unit (DAP).

An improvement on the basic concept of FIG. 2 is to include a small (in size) circuit that is located between the data acquisition and processing (DAP) unit and the implanted sensor that extends the distance of the telemetry between the patient and the DAP unit as shown in FIG. 29. This intermediate unit (IU) is battery powered. The function of the IU is the inductive telemetry measurement of the implanted sensor and then to transmit this telemetry measurement to the DAP unit via a technique that allows the signal to be received by the DAP unit across distances of greater than 5–10 cm, and preferably across the room. The signal transmission is done one of a number of ways, including inductive telemetry with a larger diameter coil in the IU, radio frequency signals, infrared signals, or ultrasound signals. The IU is placed on the skin of the human patient just to the lateral side of the eye. The IU is packaged in the form of a patch that is adhered to the skin similar to a nicotine patch, for example. In the case of animals, the IU can be tucked (surgically) just under the skin lateral to the eye on the side of the head. The IU can have either replaceable batteries or the IU can be disposable. The advantage of the system of FIG. 29 is that the implanted unit is passive, hence requiring no batteries.

Large scale prototypes were fabricated and found to function as described. The results are shown in the parent provisional application which is incorporated by reference and are referenced only for purposes of setting forth the basis for the present invention.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for determining fluid pressure within a living animal containing the fluid under pressure which comprises:
   (a) providing a wireless capacitive MEMS chip sensor comprising an inductance coil (L) and spaced apart capacitor (C) plates as an inductive-capacitive (LC) circuit, with the fluid in the animal in pressure contact with one of the capacitive plates, wherein the circuit has an element which is a series resistance which changes as a function of temperature resulting in a change of a resonant frequency response of the circuit due to temperature;
   (b) inducing a mutual inductance as an external signal into the sensor to produce the resonant frequency response as an internal signal from the sensor; and
   (c) determining the fluid pressure and temperature within the animal externally of the animal from the internal signal as a function of the resonant frequency response from the sensor resulting from a change in capacitance of the sensor due to a variation in the spacing of the plates produced by the fluid pressure, and the temperature of the fluid from the sensor resulting from the change in the series resistance.

2. The method of claim 1 wherein the plate in contact with the fluid is a P++ doped silicon membrane.

3. The method of claims 1 or 2 wherein the coil is deposited on a substrate by at least one of sputtering and electroplating.

4. The method of claim 1 wherein an antenna receives the external signal and transmits back the internal signal from the sensor through the antenna for the determining externally of the animal the fluid pressure and the temperature of the fluid.

5. The method of claim 4 wherein the antenna is connected to the inductance coil and is spaced away from the capacitor (C) plates.

6. The method of claim 1 wherein an intermediate unit (IU) which transmits the signals is provided on the animal outside of the animal to receive and then transmit the signals from the sensor to a remote data acquisition and processing unit (DAP).

7. A system for detecting increased fluid pressure in an animal which comprises:
   (a) a sensor comprising a wireless capacitive MEMS chip sensor comprising an inductance coil (L) and spaced apart capacitor (C) plates as an inductive capacitive (LC) circuit, which is adapted to be in contact with the fluid in the animal with one of the capacitive plates, wherein the circuit has an element which is a series resistance which changes as a function of temperature resulting in a change of a resonant frequency response of the circuit due to temperature; and (b) a mutual inductance producing device which measures the resonant frequency response of the sensor as an internal signal produced by the inductance device as an external signal relative to the animal, wherein the increased pressure of the fluid in the animal is detected over time as a result from a change in capacitance of the sensor due to a variation of the spacing of the plates produced by the fluid pressure and the change of the resonant frequency response of the series resistance; and (c) means for externally monitoring the fluid pressure and temperature in the animal as a function of the external signal.

8. The system of claim 7 wherein an antenna which is external of the sensor receives the external signal from the monitoring means and transmits back the internal signal externally of the animal to the monitoring means for determining the fluid pressure and temperature.

9. The system of claim 8 wherein the antenna is connected to the inductance coil and is spaced away from the capacitor (C) plates.

10. The system of claim 7 wherein the means for monitoring includes memory means for storing a series of pressure and temperature determinations for several animals.

11. The system of claim 10 wherein the memory means is a computer.

12. The system of claim 7 wherein an intermediate unit (IU) is provided on the animal outside of the animal to receive and then transmit the signals from the sensor to a remote data acquisition and processing unit (DAP).

13. A method for determining fluid pressure within an eyeball containing the fluid under pressure which comprises:

(a) providing a wireless capacitive MEMS chip sensor comprising an inductance coil (L) and spaced apart capacitor (C) plates as an inductive-capacitive (LC) circuit, with the fluid of the eye in contact with one of the capacitive plates, wherein the circuit has an element which is a series resistance which changes as a function of temperature resulting in a change of a resonant frequency response of the circuit due to temperature;

(b) inducing a mutual inductance as an external signal into The sensor to produce the resonant frequency response as an internal signal from the sensor; and (c) determining the fluid pressure and temperature within the eyeball externally of the eyeball from the internal signal as a function of the resonant frequency response from the sensor resulting from a change in capacitance of the sensor due to a variation in the spacing of the plates produced by the fluid pressure in the eyeball and the temperature of the fluid from the sensor resulting from the change in the series resistance.

14. The method of claim 13 wherein the plate in contact with the fluid is a P++ doped silicon membrane.

15. The method of claims 13 or 14 wherein the coil is deposited on a substrate by at least one of sputtering and electroplating.

16. The method of claims 13 or 14 wherein the sensor is implanted in the vitriol chamber adjacent to the cornea of the eyeball.

17. The method of claims 13 or 14 wherein the sensor is implanted in the aqueous chamber adjacent to the cornea of the eyeball.

18. The method of claim 13 wherein the pressure of the fluid is between about 10 and 20 mm of Hg (1333 to 2666 Pascal) for normal pressure of the fluid and between about 20 and 80 mm of Hg (2666 to 10,666 Pascal) for glaucoma.

19. The method of claim 13 wherein an antenna receives the external signal and transmits back the internal signal externally of the eyeball for determining the fluid pressure and temperature.

20. The method of claim 13 wherein an intermediate unit (IU) is provided on the animal outside of the eyeball to receive and then transmit the signals from the sensor to a remote data acquisition and processing unit (DAP).

21. A system for detecting increased fluid pressure and thus glaucoma of the eye which comprises:

(a) a wireless capacitive MEMS chip sensor comprising an inductance coil (L) and spaced apart capacitor (C) plates as an inductive capacitive (LC) circuit, adapted to be in contact with the fluid of the eye in contact with one of the capacitive plates, wherein the circuit has an element which is a series resistance which chances as a function of temperature resulting in a change of a resonant frequency response of the circuit due to temperature; and (b) a mutual inductance producing device which measures the resonant frequency response of the sensor as an internal signal produced by the inductance producing device as an external signal relative to the eyeball, wherein the increased pressure of the fluid in the eyeball which is to be detected by the sensor results from a change in capacitance of the sensor due to a variation of the spacing of the plates produced by the fluid pressure in the eyeball and any change of the resonant frequency response of the element in relation to temperature;

(c) means for externally monitoring the fluid pressure and temperature in the eyeball as a function of the external signal.

22. The system of claim 21 wherein an antenna is external of the sensor and receives the external signal from the monitoring means and transmits back the internal signal externally of the eyeball to the monitoring means for determining the fluid pressure and temperature.

23. The system of claim 21 wherein the means for monitoring comprises an atmospheric pressure sensor, so that a pressure in the eyeball can be determined relative to the atmospheric pressure.

24. The system of claim 21 wherein the means for monitoring includes a memory means for storing a series of eye pressure determinations for several patients.

25. The system of claim 24 wherein the memory means is a computer.

26. The system of claim 21 wherein an intermediate unit (IU) is provided on the animal outside of the eyeball to receive and then transmit the signals from the sensor to a remote data acquisition and processing unit (DAP).

27. A method for determining fluid pressure within an environment containing the fluid under pressure which comprises:

(a) providing a wireless capacitive MEMS chip sensor comprising an inductance coil (L) and spaced apart capacitor (C) plates as an inductive-capacitive (LC) circuit, with the fluid in the environment in pressure contact with one of the capacitive plates, wherein the circuit has an element which is a series resistance which changes as a function of temperature resulting in a change of a resonant frequency response of the circuit due to temperature;

(b) inducing a mutual inductance as an external signal into the sensor to produce the resonant frequency response as an internal signal from the sensor; and (c) determining the fluid pressure and temperature within the environment externally of the environment from the internal signal as a function of the resonant frequency response from the sensor resulting from a change in capacitance of the sensor due to a variation in the spacing of the plates produced by the fluid pressure and the temperature in the environment from the sensor resulting from the change in the series resistance.

28. The method of claim 27 wherein an intermediate unit (IU) to receive and then transmit signals from the sensors to a remote data acquisition and processing unit (DAP) is provided adjacent to and outside of the fluid.

29. A system for detecting increased fluid pressure in an environment which comprises:

(a) a sensor comprising a wireless capacitive MEMS chip sensor comprising an inductance coil (L) and spaced apart capacitor (C) plates as an inductive capacitive (LC) circuit, with the fluid in the environment in pressure contact with one of the capacitive plates, wherein the circuit has an element which is a series resistance which changes as a function of temperature resulting in a change of a resonant frequency response of the circuit due to temperature; and (b) a mutual inductance producing device which measures the resonant frequency response of the sensor as an internal signal produced by the inductance device as an external signal relative to the environment, wherein the pressure of the fluid in the environment which is to be detected over time results from a change in capacitance of the sensor due to a variation of the spacing of the plates produced by the fluid pressure and a determination of the temperature of the fluid from the sensor from the change in the series resistance; and (c) means for externally monitoring the fluid pressure and the temperature in the environment as a function of the external signal.

* * * * *

UNITED STATES PATENT AND TRADEMARK OFFICE
CERTIFICATE OF CORRECTION

PATENT NO. : 6,890,300 B2
DATED : May 10, 2005
INVENTOR(S) : John R. Lloyd et al.

It is certified that error appears in the above-identified patent and that said Letters Patent is hereby corrected as shown below:

Column 15,
Line 45, "The sensor" should be -- the sensor --.

Column 16,
Line 17, "chances" should be -- changes --.

Signed and Sealed this

Eighteenth Day of October, 2005

JON W. DUDAS
*Director of the United States Patent and Trademark Office*